United States Patent
Muguruma et al.

(10) Patent No.: US 11,136,612 B2
(45) Date of Patent: Oct. 5, 2021

(54) REAGENT FOR GLUCOSE SENSOR, GLUCOSE SENSOR, METHOD FOR MANUFACTURING GLUCOSE SENSOR, AND GLUCOSE MEASURING DEVICE

(71) Applicant: NATIONAL INSTITUTE OF ADVANCED INDUSTRIAL SCIENCE AND TECHNOLOGY, Tokyo (JP)

(72) Inventors: Hitoshi Muguruma, Tokyo (JP); Atsunori Hiratsuka, Tsukuba (JP); Hisanori Iwasa, Tsukuba (JP); Jun Takagi, Nagaokakyo (JP); Hiroyasu Kadoya, Nagaokakyo (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 26 days.

(21) Appl. No.: 16/325,847

(22) PCT Filed: Aug. 7, 2017

(86) PCT No.: PCT/JP2017/028621
§ 371 (c)(1),
(2) Date: Feb. 15, 2019

(87) PCT Pub. No.: WO2018/043050
PCT Pub. Date: Mar. 8, 2018

(65) Prior Publication Data
US 2019/0194714 A1 Jun. 27, 2019

(30) Foreign Application Priority Data
Aug. 29, 2016 (JP) .............................. JP2016-166929

(51) Int. Cl.
*G01N 27/327* (2006.01)
*C12Q 1/00* (2006.01)
(Continued)

(52) U.S. Cl.
CPC ............ *C12Q 1/006* (2013.01); *C01B 32/158* (2017.08); *C12M 1/40* (2013.01); *C12N 9/0006* (2013.01);
(Continued)

(58) Field of Classification Search
CPC ... G01N 27/327–3272; G01N 27/3278; C12Q 1/006
See application file for complete search history.

(56) References Cited

U.S. PATENT DOCUMENTS

| 7,052,591 B2 * | 5/2006 | Gao ....................... C12Q 1/004 204/490 |
| 2005/0186333 A1 * | 8/2005 | Douglas ................. B82Y 30/00 427/97.1 |

(Continued)

FOREIGN PATENT DOCUMENTS

| EP | 2821497 A2 | 1/2015 |
| EP | 2845908 A1 | 3/2015 |

(Continued)

OTHER PUBLICATIONS

Chen et al., "Effect of Surfactant Type and Redox Polymer Type on Single-Walled Carbon Nanotube Modified Electrodes," Langmuir 2013, 29, 10586-10595 (Year: 2013).*

(Continued)

*Primary Examiner* — Alexander S Noguerola
(74) *Attorney, Agent, or Firm* — Oliff PLC

(57) ABSTRACT

A reagent used for a glucose sensor for electrochemical, quantitative determination of glucose, includes a flavin (Continued)

adenine dinucleotide glucose dehydrogenase, single-walled carbon nanotubes, and a dispersant.

14 Claims, 13 Drawing Sheets

(51) Int. Cl.
*C12M 1/40* (2006.01)
*G01N 27/416* (2006.01)
*C12Q 1/32* (2006.01)
*C01B 32/158* (2017.01)
*C12N 9/04* (2006.01)
*B82Y 30/00* (2011.01)
*B82Y 40/00* (2011.01)

(52) U.S. Cl.
CPC ............. *C12Q 1/32* (2013.01); *G01N 27/327* (2013.01); *G01N 27/3272* (2013.01); *G01N 27/3278* (2013.01); *G01N 27/416* (2013.01); *B82Y 30/00* (2013.01); *B82Y 40/00* (2013.01); *C01B 2202/02* (2013.01); *C12Y 101/01022* (2013.01)

(56) References Cited

U.S. PATENT DOCUMENTS

| | | | |
|---|---|---|---|
| 2008/0220460 | A1 | 9/2008 | Kawaminami et al. |
| 2009/0084678 | A1 | 4/2009 | Joshi et al. |
| 2010/0187107 | A1* | 7/2010 | Katsuki .................. C12Q 1/001 204/403.14 |
| 2013/0087455 | A1* | 4/2013 | Lee .................... G01N 27/3272 204/403.03 |
| 2014/0353154 | A1 | 12/2014 | Joshi et al. |
| 2015/0064733 | A1 | 3/2015 | Duefel et al. |
| 2015/0101929 | A1 | 4/2015 | Jung et al. |
| 2015/0129425 | A1 | 5/2015 | Tsukada et al. |
| 2015/0192537 | A1 | 7/2015 | Sekimoto |

FOREIGN PATENT DOCUMENTS

| | | |
|---|---|---|
| JP | 2007-039623 A | 2/2007 |
| JP | 2015-517302 A | 6/2015 |
| JP | 2015-519892 A | 7/2015 |
| WO | 2008/059777 A1 | 5/2008 |
| WO | 2013/164477 A1 | 11/2013 |
| WO | 2014/002998 A1 | 1/2014 |
| WO | 2014/002999 A1 | 1/2014 |

OTHER PUBLICATIONS

Yang et al., "Efficient Expression, Purification, and Characterization of a Novel FAD-Dependent Glucose Dehydrogenase from Aspergillus terreus in Pichia pastoris," J. Microbiol. Biotechnol. (2014), 24(11), 1516-1524 (Year: 2014).*
Zafar et al., "Characterization of different FAD-dependent glucose dehydrogenase for possible use in glucose-based biosensors and biofuel cells," Anal. Bioanal. Chem. (2012) 402:2069-2077 (Year: 2012).*
Yoshida et al., "Structural analysis of fungus-derived FAD glucose dehydrogenase," Nature-Scientific Reports 5-13498, published Aug. 27, 2015, including supplemental information (Year: 2015).*
Muguruma et al.; "Electronically Type-Sorted Carbon Nanotube-Based Electrochemical Biosensors with Glucose Oxidase and Dehydrogenase"; ACS Applied Materials & Interface; vol. 7, 2014; pp. 584-592.
Hoshino et al.; "Amperometric biosensor based on multilayer containing carbon nanotube, plasma-polymerized film, electron transfer mediator phenothiazine, and glucose dehydrogenase"; Bioelectrochemistry; vol. 84; May 2011; pp. 1-5.
Ozawa et al.; "Identification and characterization of thermostable glucose dehydrogenases from *Thermophilic filamentous* fungi"; Appl Microbiol Biotechnol; vol. 101; Aug. 2016; pp. 173-183.
Iwasa et al.; "Thermostable FAD-dependent Glucose Dehydrogenases from *Thermophilic filamentous* Fungus *Thermoascus aurantiacus*"; Electrochemistry; vol. 84; May 2016; pp. 342-348.
Iwasa et al.; "Thermophilic Talaromyces emersonii Flavin Adenine Dinucleotide-Dependent Glucose Dehydrogenase Bioanode for Biosensor and Biofuel Cell Applications"; ACS Omega; vol. 2; 2017; pp. 1660-1665.
Sekiguchi et al., "Biosensor With Carbon Nanotube, Plasma-Polymerized Thin Film"; The Institute of Electronics, Information and Communication Engineers; IEICE Technical Report; pp. 15-18, Feb. 2011.
Oct. 31, 2017 International Search Report issued in International Patent Application No. PCT/JP2017/028621.
Jan. 8, 2020 Search Report issued in European Patent Application No. 17846059.8.
Jun. 23, 2020 Office Action issued in Japanese Patent Application No. 2016-166929.

* cited by examiner

FIG.10
(a) EXAMPLE 1
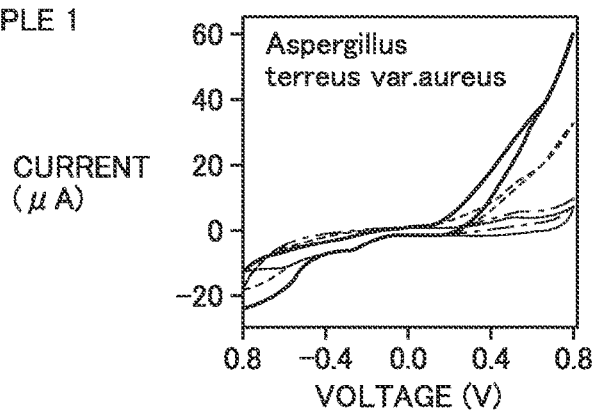
(b) COMPARATIVE EXAMPLE 1
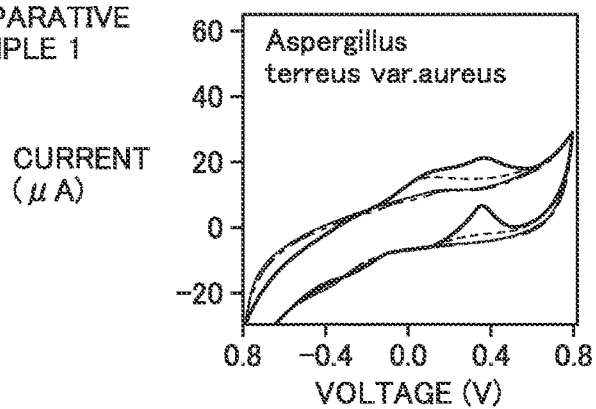
(c) COMPARATIVE EXAMPLE 2
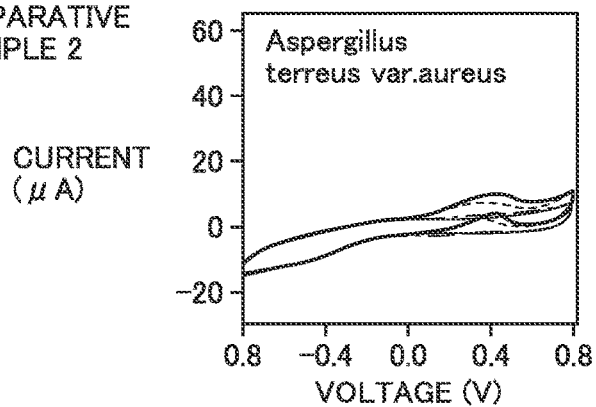
```
———— 0mM  (GLUCOSE CONCENTRATION)
— — — 2.5mM
------ 14mM
———— 48mM
```

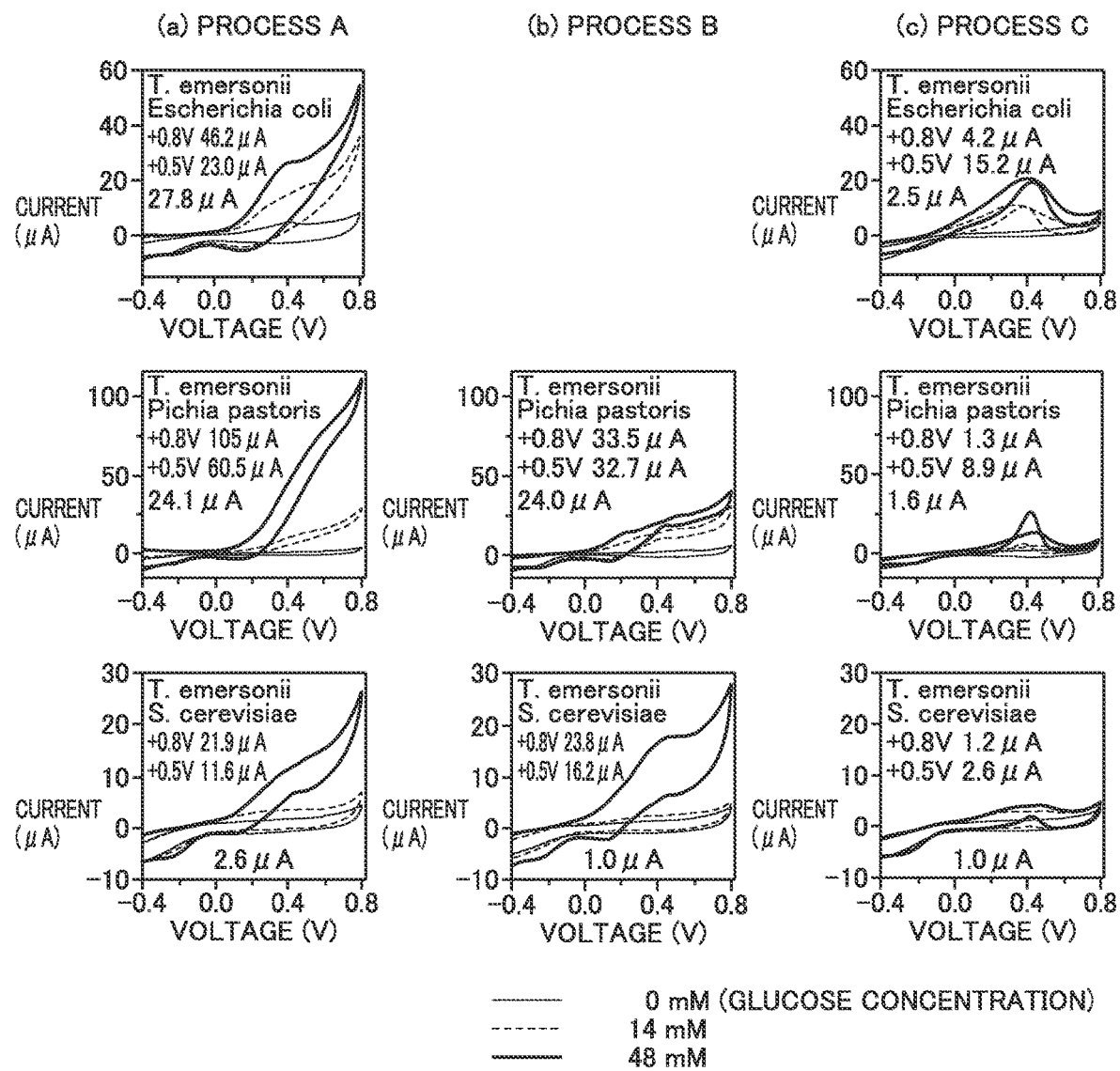

REAGENT FOR GLUCOSE SENSOR, GLUCOSE SENSOR, METHOD FOR MANUFACTURING GLUCOSE SENSOR, AND GLUCOSE MEASURING DEVICE

TECHNICAL FIELD

The present invention relates to a reagent for a glucose sensor, the glucose sensor, a method for manufacturing the glucose sensor, and a glucose measuring device.

BACKGROUND ART

A glucose sensor such as a blood sugar level sensor using electrochemistry is known. Generally, such a glucose sensor includes two or more electrodes at least including a working electrode and a counter electrode, and after a spacer for forming a cavity is bonded on the electrodes, a reagent layer including an enzyme, a mediator and the like is formed at a portion of the cavity, and a cover is attached to structure the glucose sensor.

When a specimen (blood, interstitial fluid, sweat, etc.) is introduced into the cavity of the glucose sensor (a space formed by a groove formed in the spacer), the glucose (or a substrate) contained in the specimen reduces the mediator (or an electrode active material) via the enzyme. Here, when a predetermined voltage is applied to the electrode, the reduced mediator is oxidized by an electrochemical reaction. When the reduced mediator is oxidized, an oxidation current is generated, and the amount of the glucose can be detected by measuring this oxidation current.

Furthermore, using electrically conductive fine particles such as carbon nanotubes (hereinafter also abbreviated as "CNTs") to measure a current generated by direct electron transfer between a glucose-bound enzyme and an electrode through the CNTs to measure a glucose level, is also considered.

For example, Patent Literature 1 (WO2014/002999) discloses a reagent layer for a glucose sensor including an oxidoreductase, a water-soluble electrically conductive polymer and electrically conductive fine particles. Patent Literature 1 discloses using flavin adenine dinucleotide-dependent glucose dehydrogenase (hereinafter also abbreviated as "FAD-GDH") as the oxidoreductase.

Furthermore, Patent Literature 2 (WO2014/002998) discloses a reagent layer for a glucose sensor including an enzyme, electrically conductive fine particles and a non-electrically conductive polymer. Patent Literature 2 discloses using CNTs as the electrically conductive fine particles.

Non-Patent Literature 1 (Muguruma et al., IEICE technical report, Organic Electronics 110 (409), pp. 15-18, Jan. 31, 2011) specifically discloses using CNT as a mediator in a reagent layer of a glucose sensor (a reagent for a glucose sensor).

CITATION LIST

Patent Literature

PTL 1: WO2014/002999
PTL 2: WO2014/002998

Non Patent Literature

NPL 1: Muguruma et al., IEICE technical report, Organic Electronics 110 (409), pp. 15-18, Jan. 31, 2011

SUMMARY OF INVENTION

Technical Problem

However, the present inventors have found through an investigation that when FAD-GDH is used as the enzyme, direct electron transfer may not occur in some case depending on the type of CNT.

The present invention has been made in view of the above problem, and it is an object of the present invention to provide a glucose sensor which is highly sensitive and accurate when CNT is used and FAD-GDH is used as an enzyme.

Solution to Problem

[1]
A reagent used for a glucose sensor for electrochemical, quantitative determination of glucose, comprising
a flavin adenine dinucleotide glucose dehydrogenase (FAD-GDH), single-walled carbon nanotubes (CNTs), and a dispersant.

[2]
The reagent for a glucose sensor according to item [1], wherein the flavin adenine dinucleotide glucose dehydrogenase is glycosylated.

[3]
The reagent for a glucose sensor according to item [2], wherein the flavin adenine dinucleotide glucose dehydrogenase has a molecular weight of 90 KDa or more.

[4]
The reagent for a glucose sensor according to item [3], wherein the flavin adenine dinucleotide glucose dehydrogenase has a molecular weight of 110 KDa or more.

[5]
The reagent for a glucose sensor according to any one of items [1] to [4], wherein the dispersant includes at least one type of compound selected from an anionic compound, a cationic compound, and a nonionic compound.

[6]
The reagent for a glucose sensor according to item [5], wherein the anionic compound is at least any one of sodium dodecyl sulfate, sodium cholate and sodium dodecylbenzene sulfonate.

[7]
The reagent for a glucose sensor according to item [5] or [6], wherein the cationic compound is cetyltrimethylammonium bromide.

[8]
The reagent for a glucose sensor according to any one of items [5] to [7], wherein the nonionic compound is at least any one of octylphenol ethoxylate and polysorbates.

[9]
The reagent for a glucose sensor according to any one of items [1] to [8], wherein the flavin adenine dinucleotide glucose dehydrogenase is derived from *Aspergillus filamentous* fungi, *Thermoascus filamentous* fungi or *Talaromyces filamentous* fungi.

[10]
A sensor for electrochemical, quantitative determination of glucose, comprising
an electrode,
the electrode having a surface at least partially covered with a reagent layer comprising a reagent according to any one of items [1] to [9].

[11]

A method for manufacturing a glucose sensor according to item [10], applying on the electrode a carbon nanotube liquid containing the single-walled carbon nanotubes and the dispersant, followed by an enzyme liquid containing the flavin adenine dinucleotide glucose dehydrogenase, and drying them to form the reagent layer.

[12]

The method for manufacturing a glucose sensor according to item [10], applying on the electrode an enzyme liquid containing the flavin adenine dinucleotide glucose dehydrogenase, followed by a carbon nanotube liquid containing the single-walled carbon nanotubes and the dispersant, and drying them to form the reagent layer.

[13]

The method for manufacturing a glucose sensor according to item [10], applying on the electrode a liquid mixture of a carbon nanotube liquid containing the single-walled carbon nanotubes and the dispersant and an enzyme liquid containing the flavin adenine dinucleotide glucose dehydrogenase, and drying it to form the reagent layer.

[14]

A glucose measuring device using the glucose sensor according to item [10].

Advantageous Effects of Invention

The present invention can thus provide a glucose sensor which is highly sensitive and accurate when CNT is used and FAD-GDH is used as an enzyme.

BRIEF DESCRIPTION OF DRAWINGS

FIG. 10 is a graph showing a result of measuring a value of a current in Test Example 1.

FIG. 13 is another graph showing a result of measuring a value of a current in Test Example 2.

DESCRIPTION OF EMBODIMENTS

Figure 1:
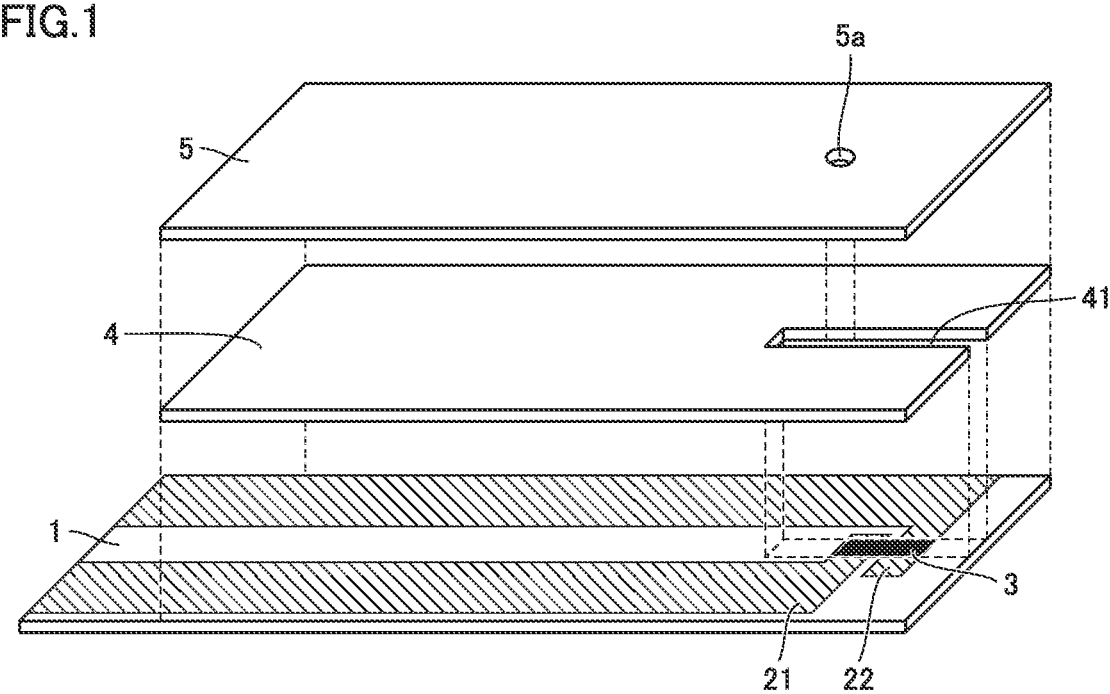
FIG. 1 is an exploded perspective view showing a configuration of a glucose sensor according to a first embodiment.

Hereinafter, an embodiment of the present invention will be described with reference to the drawings. In the drawings, identical reference characters denote identical or equivalent components. Dimensional relationships such as length, width, thickness, depth, and the like have been appropriately changed for clarification and simplification of the drawings, and do not represent actual dimensional relationships. It is needless to say that each embodiment is an example and partial substitution or combination of configurations shown in different embodiments is possible.

First Embodiment

With reference to FIG. 1, a glucose sensor of the present embodiment is a glucose sensor (a sensor chip) for measuring glucose (a substrate) contained in a sample liquid, and includes an insulating substrate 1, an electrode, a reagent layer 3, a spacer 4, and a cover 5.

The electrode includes a working electrode 21 and a counter electrode 22 provided on one surface of insulating substrate 1. Reagent layer 3 is formed on a portion of a surface of the electrode facing away from insulating substrate 1.

Spacer 4 has a notch 42 for forming a cavity 41 for guiding a sample liquid to reagent layer 3, and spacer 4 is disposed on the electrode so that reagent layer 3 is located inside notch 42 (or cavity 41). Preferably, of the surface of the electrode, at least a portion exposed in cavity 41 is covered with the reagent layer.

Cover 5 is provided on a surface of spacer 4 facing away from insulating substrate 1 so as to cover at least notch 42. Cover 5 has an air hole 5a in communication with cavity 41.

In the present embodiment, reagent layer 3 is composed of a reagent (a reagent for a glucose sensor) including flavin adenine dinucleotide glucose dehydrogenase (FAD-GDH), single-walled carbon nanotubes (single-walled CNTs), and a dispersant.

The present inventors have conducted an inspection to find that in a glucose sensor using FAD-GDH as an enzyme, when a multi-walled CNT or bundled single-walled CNTs is/are used as CNT, direct electron transfer between the enzyme and the electrode via the CNT does not easily occur. On the other hand, it has been found that direct electron transfer occurs when debundled single-walled CNTs are used.

It is inferred that these result because FAD-GDH (or an enzyme 33) has an active center having a size of around 1 nm and when a multi-walled CNT or bundled single-walled CNTs having a particle size larger than that is/are used, CNT 31 cannot enter the active center (see FIGS. 9(b) and 9(c)), and CNT 31 cannot pass/receive electrons to/from enzyme 33. On the other hand, it is inferred that when debundled single-walled CNTs are used, (i.e., when single-walled CNTs and a dispersant are blended in the reagent liquid), CNT 31 can enter the active center of enzyme 33 (see FIG. 9(a)), and CNT 31 can pass/receive electrons to/from enzyme 33.

Therefore, when FAD-GDH is used as an enzyme, using debundled single-walled CNTs (a reagent liquid containing single-walled CNTs and a dispersant) allows a glucose sensor to be provided which is highly sensitive and accurate using CNT as a mediator.

In a relation in size with the active center of FAD-GDH, the single-walled CNT preferably has an outer diameter (or the cylinder has a diameter) of 0.75 to 2.0 nm, more preferably 0.75 to 1.7 nm. The particle diameter of the single-walled CNT can be measured with a transmission electron microscope (TEM) or an atomic force microscope (AFM).

Note, for example, that the electrode may have a surface with a hydrophilic polymer membrane formed thereon. This is because when the electrode (or an electrode membrane) has a surface covered with the reagent layer, the hydrophilic polymer membrane allows the electrode to have a surface enhanced in wettability by the reagent liquid and thus helps to form the reagent layer. The hydrophilic polymer membrane for example includes an acetonitrile plasma-polymerized membrane, a membrane composed of a hydrophilic polymer such as carboxymethyl cellulose and methyl cellulose or an amphiphilic polymer such as polyvinyl pyrrolidone or the like.

Preferably, FAD-GDH is glycosylated (i.e., has a carbohydrate attached). The glycosylated FAD-GDH suppresses detachment of the reagent layer and suppresses deactivation of the enzyme (or FAD-GDH).

In the process for forming the reagent layer, when introducing fine particles such as CNTs, a reagent layer such as an enzyme may peel off due to the fine-particle layer's membrane stress. When the reagent peels off, direct electron transfer between the enzyme and the electrode via the CNT is not performed effectively. In addition, produced sensors have large variation in quality, characteristics, and the like.

In addition, when the CNT liquid is brought into contact with the enzyme, the enzyme may be inactivated due to an effect of the dispersant contained in the CNT liquid.

In contrast, when FAD-GDH is glycosylateed, the enzyme's three-dimensional structure is rigidly held. This can suppress detachment of the reagent layer when with the enzyme as a base the CNT liquid is dropped to form the reagent layer. As a result, direct electron transfer between the enzyme and the electrode via the CNT can be performed effectively. This reduces variation between produced sensors in quality, characteristics, and the like.

In addition, when the CNT liquid is brought into contact with the enzyme, and the dispersant or the CNT acts on the enzyme, the enzyme having its three-dimensional structure rigidly held by a carbohydrate is not inactivated and its original activity can be ensured.

As the FAD-GDH a FAD-GDH derived for example from *Aspergillus filamentous* fungi, *Thermoascus filamentous* fungi or *Talaromyces filamentous* fungi can suitably be used (see, for example, Japanese Patent Laying-Open Nos. 2015-167506, 2016-007191, 2016-007192, and 2016-007193).

The dispersant is not particularly limited insofar as it is a compound which can prevent bundling of single-walled CNTs. The dispersant can for example be at least one type of compound selected from an anionic compound, a cationic compound and a nonionic compound.

The anionic compound is sodium dodecyl sulfate, sodium cholate or sodium dodecylbenzene sulfonate, for example. The cationic compound is cetyltrimethylammonium bromide for example. The nonionic compound is octylphenol ethoxylate (Triton-X-100, Triton-X-114, Triton-X-305, Triton-X-405 and the like produced by Dow Chemical Company), or polysorbates (polysorbate 20 (Tween 20), polysorbate 40 (Tween 40), polysorbate 60 (Tween 60), polysorbate 80 (Tween 80), etc.), for example.

Reagent layer 3 may include a hydrophilic polymer (carboxymethylcellulose or the like). Such a hydrophilic polymer effectively helps to immobilize reagent layer 3 to a surface of the electrode or filters impurity (such as blood cells in the blood) in a sample liquid.

While insulating substrate 1 is not particularly limited in what material is used to form it, it is formed of plastic materials such as PET (polyethylene terephthalate) film, photosensitive materials, paper, glass, ceramics, biodegradable materials, or the like. These materials are also used as materials for spacer 4 and cover 5.

An electrode provided on insulating substrate 1 includes at least working electrode 21 and counter electrode 22. In addition to working electrode 21 and counter electrode 22, the electrode may include a reference electrode serving as a reference for potential in measuring the electrode's potential and a detection electrode for detecting that a sample is supplied to cavity 41.

These electrodes (the working, counter, reference, and detection electrodes, etc.) are formed of materials such as platinum, gold, palladium or a similar noble metal, carbon, copper, aluminum, nickel, titanium, ITO (indium tin oxide), ZnO (zinc oxide), and the like.

Cover 5 is preferably formed of an insulating material, and it can for example be plastics such as PET film, photosensitive materials, paper, glass, ceramics, and biodegradable materials. It is preferable that cover 5 have air hole 5a in communication with cavity 41 formed by spacer 4. This is because capillarity allows a sample to be attracted toward air hole 5a and thus helps introducing the sample into cavity 41.

<Method for Manufacturing Glucose Sensor>

An example of a method for manufacturing the glucose sensor of the present embodiment will be described with reference to FIGS. 1 to 6. FIG. 1 is an exploded perspective view showing a configuration of a glucose sensor according to the present embodiment. FIGS. 2 to 6 are diagrams for illustrating an example of a process for manufacturing the glucose sensor of the present embodiment, and each shows a different step. In this embodiment, a plurality of glucose sensors can be fabricated at the same time.

Figure 2:
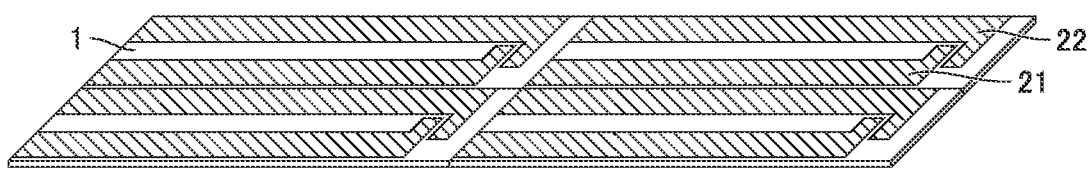
FIG. 2 is a perspective view for illustrating an example of a process for manufacturing a glucose sensor of the first embodiment.

Initially, referring to FIG. 2, an electrode (working electrode 21 and counter electrode 22 for quantitatively determining a substrate) is formed on each of a plurality of insulating substrates 1. Specifically, an electrically conductive layer is formed on one surface of insulating substrate 1 by sputtering or the like, and the formed electrically conductive layer is subjected to laser-processing, photolithography, or the like to form a pattern to thus form the electrode (or electrode membrane). Other than working electrode 21 and counter electrode 22, the reference electrode, detection electrode, and the like mentioned above may be formed. A plasma treatment may be applied to the surface of the electrode and that of insulating substrate 1.

The electrode membrane can be formed, for example, by a sputtering method, a vacuum deposition method, an ion plating method, a CVD (chemical vapor deposition) method, an MBE (molecular beam epitaxy) method, a melt transporting method, a melt temperature lowering method, a sol-gel method, a plating method, a coating method, screen-printing, or the like. While the electrode membrane is not particularly limited in thickness, it is for example 5 to 500 nm.

Figure 3:
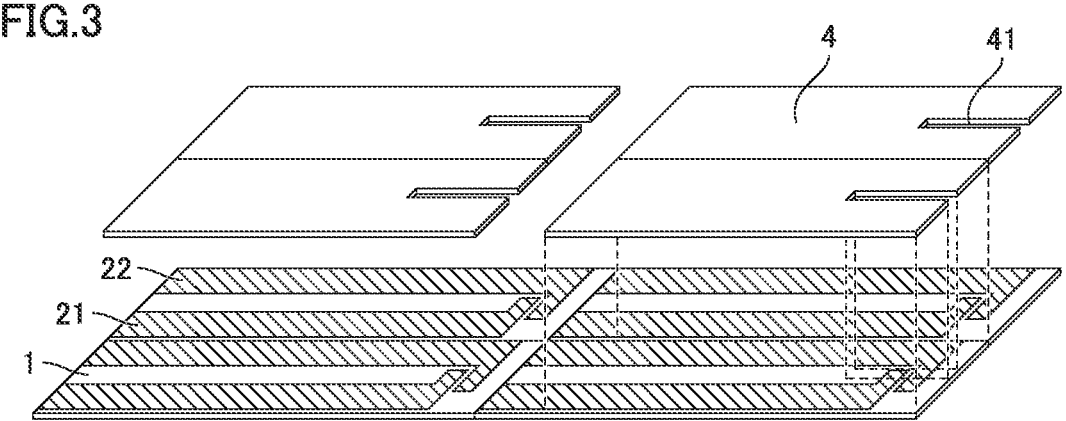
FIG. 3 is another perspective view for illustrating the example of the process for manufacturing the glucose sensor of the first embodiment.

Subsequently, referring to FIG. 3, spacer 4 having notch 42 is bonded to a portion of the electrode (working electrode 21 and counter electrode 22) on a side thereof facing away from insulating substrate 1, and a portion of a surface of insulating substrate 1 on a side facing the electrode in a region in which the electrode is not formed.

[Reagent Layer Formation Process]

Figure 4:
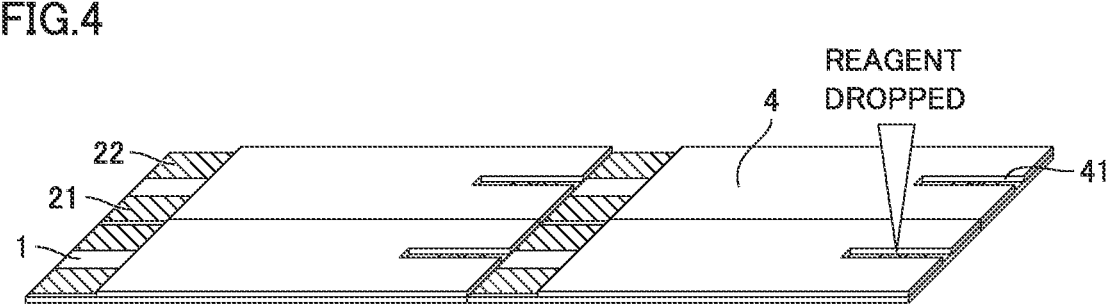
FIG. 4 is another perspective view for illustrating the example of the process for manufacturing the glucose sensor of the first embodiment.

Referring to FIG. 4, a reagent liquid including an enzyme (FAD-GDH), single-walled CNTs and a dispersant can be dropped on a side of the electrode (working electrode 21 and counter electrode 22) facing away from insulating substrate 1 (in notch 42) and dried to form reagent layer 3.

(Process A)

More specifically, referring to FIG. 11(a), for example, reagent layer 3 can be formed through a process in which a carbon nanotube (CNT) liquid (CNT 31 and a dispersant 32) and subsequently, an enzyme liquid (enzyme 33) are applied on an electrode 2 (a hydrophilic polymer membrane 20) (process A).

(Process B)

Referring to FIG. 11(b), reagent layer 3 may be formed through a process in which the enzyme liquid (enzyme 33) is applied prior to the CNT liquid (CNT 31 and dispersant 32) (process B).

(Process C)

Referring to FIG. 11(c), reagent layer 3 may be formed through a process in which initially the CNT liquid (CNT 31 and dispersant 32) and the enzyme liquid (enzyme 33) are mixed together to prepare a liquid mixture which is in turn applied to electrode 2 (hydrophilic polymer membrane 20) (Process C).

Figure 5:
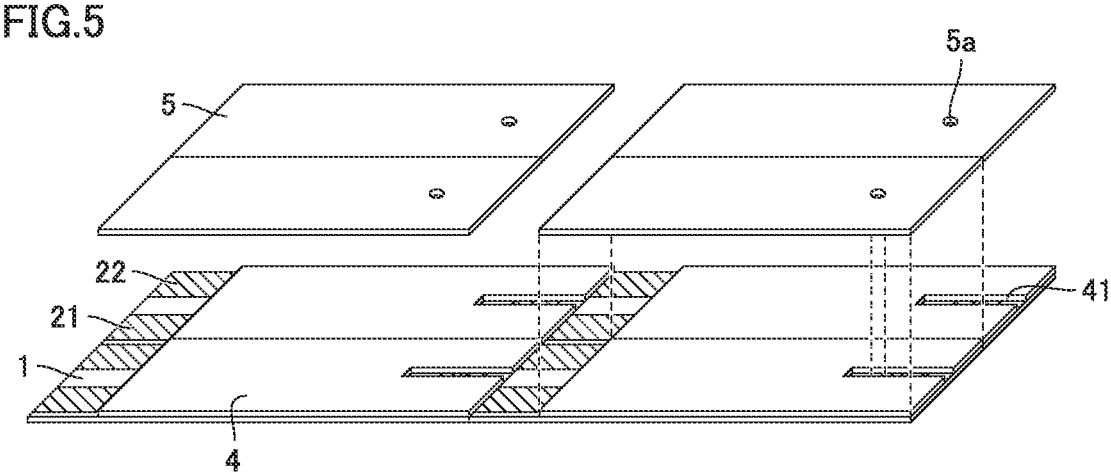
FIG. 5 is another perspective view for illustrating the example of the process for manufacturing the glucose sensor of the first embodiment.

Subsequently, referring to FIG. 5, cover 5 having air hole 5a is disposed on spacer 4 so as to cover at least notch 42 to thus form cavity 41 for guiding a sample liquid to reagent layer 3. Air hole 5a is provided on a side opposite to an opening of cavity 41 in communication with an interior of cavity 41.

Figure 6:
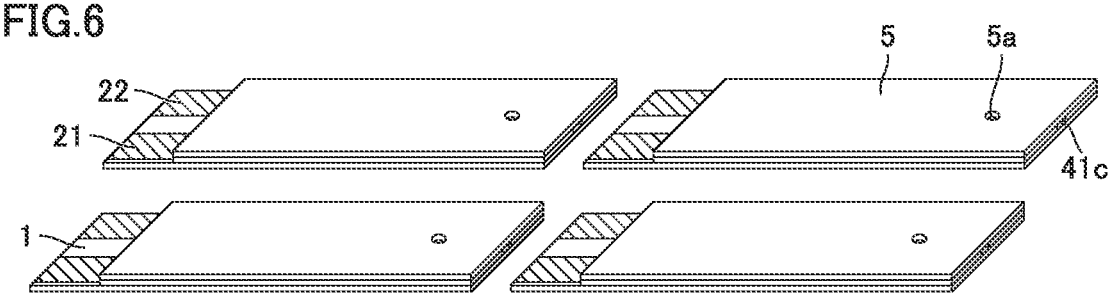
FIG. 6 is another perspective view for illustrating the example of the process for manufacturing the glucose sensor of the first embodiment.

Subsequently, a set of substrates of glucose sensors formed through the above process are divided to provide glucose sensors having cavity 41 (see FIGS. 6 and 1).

<Usage of Glucose Sensor>

The glucose sensor (or sensor chip) of the present invention is attached to a measuring instrument in use. That is, when a sample (blood or the like) is supplied to cavity 41 of the glucose sensor attached to the measuring instrument, a substance in the sample to be measured (i.e., glucose) is bound to the enzyme (FAD-GDH) and electrons are transferred by the tunnel effect to a CNT significantly close to the FAD serving as an active center, and an electric current is thus generated. The measuring instrument electrically connected to working electrode 21 and counter electrode 22 of the glucose sensor measures the current to thus quantitatively determine the substance contained in the sample to be measured.

Hereinafter, an example of usage of the glucose sensor of the present invention will be described. Initially, blood is brought into contact with an end portion (an inlet 41c) of cavity 41, and introduced into cavity 41 through capillarity. Then, a voltage is applied between working electrode 21 and counter electrode 22, and a value of a current is measured, as timed as determined. The applied voltage is, for example, 0.3 V. When blood is introduced into cavity 41, an analyte in the blood allows the enzyme and the CNT to directly transfer electrons. The current flowing when a voltage is applied between working electrode 21 and counter electrode 22 has a correlation with the analyte's concentration.

Subsequently, a value of the current is measured after the voltage is applied when a predetermined period of time has elapsed. For example, a value of the current after a period of 3 to 5 seconds has elapsed is measured. This value of the current can be used to determine the analyte's concentration from a previously obtained calibration curve.

EXAMPLES

Hereinafter, while the present invention will be described more specifically with reference to examples, the present invention is not limited thereto.

Example 1

Basically, a glucose sensor having the structure as shown in FIG. 1 described in the first embodiment was fabricated. The electrode was formed of gold. A metal film made of gold was formed by sputtering and patterned to form the electrode (the working electrode and the counter electrode). In addition, an acetonitrile plasma-polymerized membrane was applied on a surface of the electrode (that is, a portion where the reagent layer was formed). No reference or detection electrode was fabricated.

The enzyme liquid was an aqueous dispersion of FAD-GDH. The FAD-GDH was an FAD-GDH having an enzyme No. 1 shown in Table 1.

The CNT liquid was a dispersion liquid containing 0.15% by mass of single-walled CNTs (debundled and having an outer diameter of 1.1 to 1.7 nm) and 2.0% by mass of a dispersant (sodium cholate) with water used as a dispersion medium.

Figure 8:
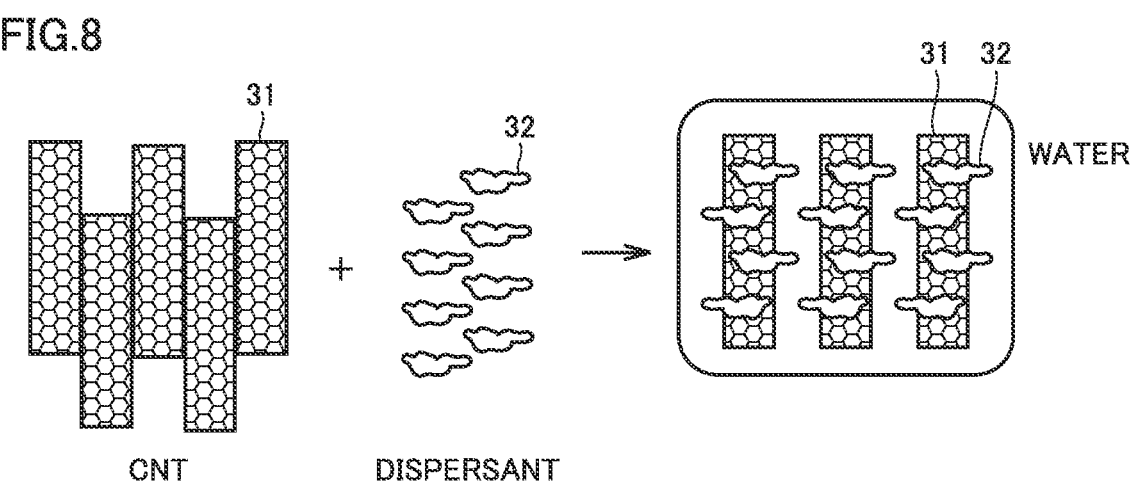
FIG. 8 is a schematic diagram for illustrating an effect of a dispersant in a carbon nanotube (CNT) liquid of Example 1.

With reference to FIG. 8, in the case of such a CNT liquid, even when bundled single-walled CNTs 31 are added, single-walled CNTs 31 are debundled due to the presence of dispersant 32. For obtaining such a single-walled CNT, and preparing such a CNT liquid, etc., for example, reference can be made to Non-Patent Literature 1.

Figure 7:
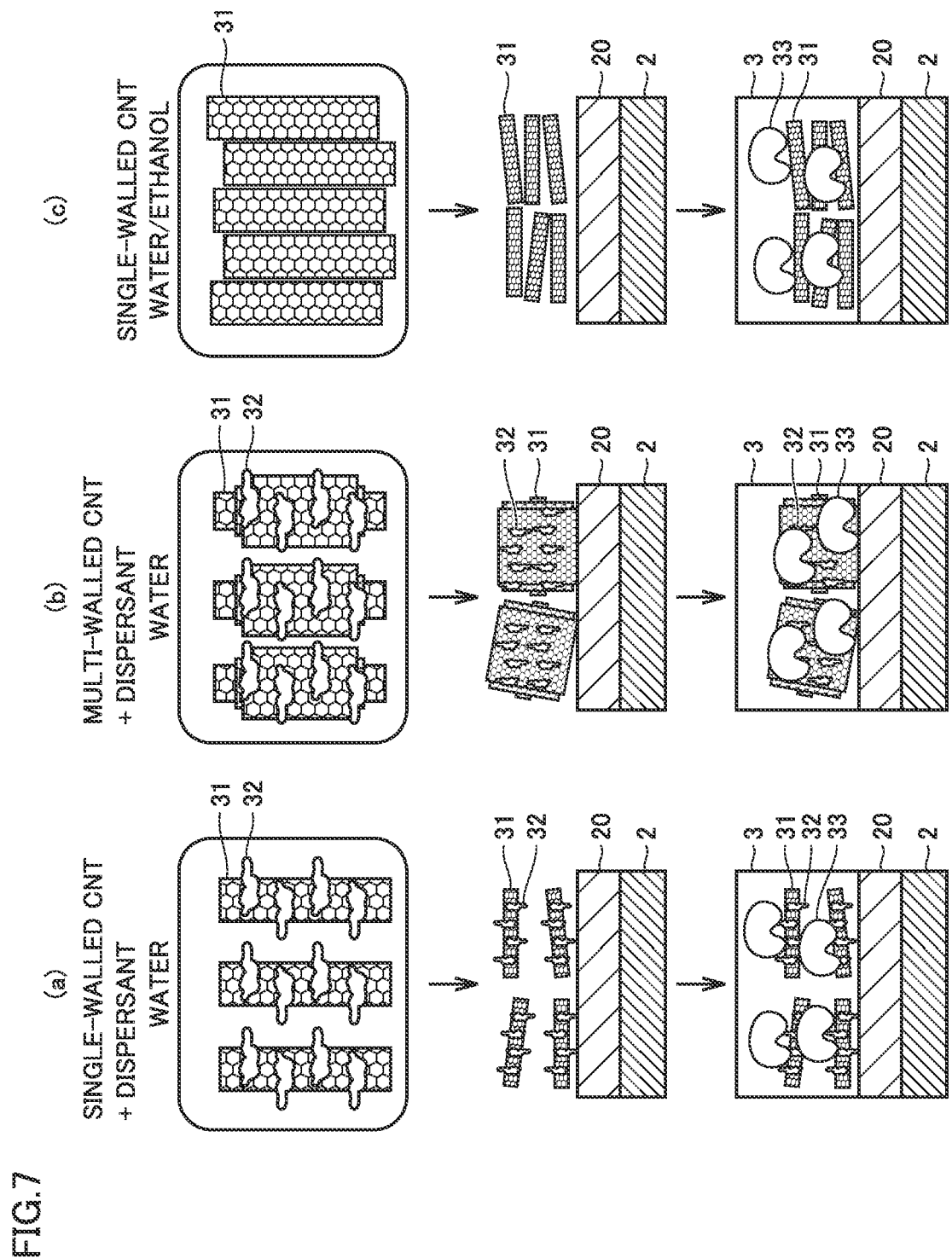
FIG. 7 is a schematic diagram showing a process for forming a reagent layer in each of Example 1, Comparative Example 1, and Comparative Example 2.

Then, as shown in FIG. 7(a), the CNT liquid (including single-walled CNTs 31 and dispersant 32) and subsequently, the enzyme liquid (including enzyme 33) are dropped on electrode 2 (hydrophilic polymer membrane 20) and dried to form reagent layer 3 (Process A).

Comparative Example 1

A glucose sensor of Comparative Example 1 was fabricated in a manner similar to that for Example 1 except that the CNT liquid was a dispersion liquid containing 0.1% by mass of multi-walled CNTs (debundled and having an outer diameter of 10 to 15 nm and 5 to 15 layers) and 2.0% by mass of a dispersant (sodium cholate) with water used as a dispersion medium. Reagent layer 3 was formed through the same process as in Example 1 shown in FIG. 7(b) (process A).

Comparative Example 2

A glucose sensor of Comparative Example 2 was fabricated in a manner similar to that for Example 1 except that no dispersant was added to the CNT liquid. That is, in Comparative Example 2, the CNT liquid was a dispersion liquid containing 0.15% by mass of single-walled CNTs (bundled) and no dispersant with a liquid mixture of water and ethanol (water:ethanol=50:50) used as a dispersion medium. Reagent layer 3 was formed through the same process as in Example 1 shown in FIG. 7(c) (process A).

Test Example 1

A liquid in which glucose was dissolved in a 20 mM phosphate buffer liquid (pH: 7.4) was prepared as a sample liquid (a glucose liquid) to be measured. The glucose's concentration was 0, 2.5, 14 or 48 mM.

This sample liquid was supplied into the cavity of each glucose sensor fabricated in Example 1, Comparative Example 1 and Comparative Example 2, and cyclic voltammetry was employed (scanning speed: 0.05 V/$_s$) to measure a value of a current passing between the working electrode and the counter electrode.

A result of the measurement of the value of the current is shown in FIG. 10. FIGS. 10($a$), 10($b$) and 10($c$) correspond to Example 1, Comparative Example 1 and Comparative Example 2, respectively.

As shown in FIG. 10 (see a value for a voltage of 0.8 V in particular), when debundled multi-walled CNT (Comparative Example 1) and bundled CNTs (Comparative Example 2 are used, an electrochemical reaction (a current) depending on glucose concentration could not be detected. In contrast, when debundled single-walled CNTs (a reagent liquid containing single-walled CNTs and a dispersant) was used (Example 1), a current was detected.

Figure 9:
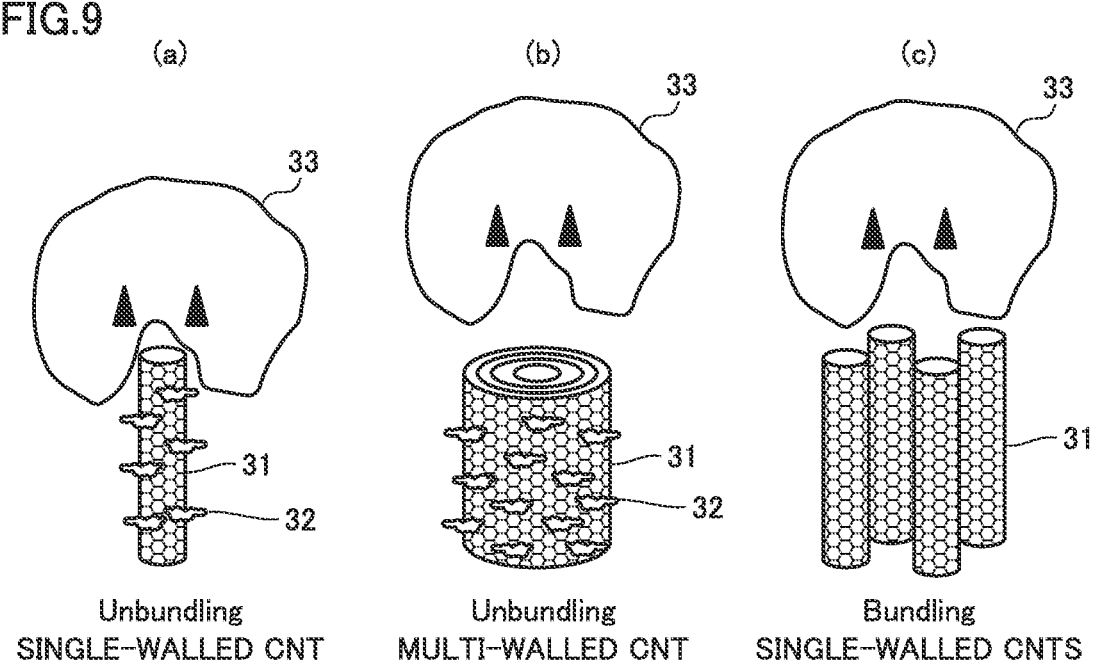
FIG. 9 is a schematic diagram for illustrating a relationship between an active center of FAD-GDH and the size of CNT.

It is inferred that this is because, with reference to FIGS. 9($b$) and 9($c$), the FAD-GDH (or enzyme 33) has an active center (located between two solid triangles) having a size of around 1 nm and when multi-walled CNT 31 (FIG. 9($b$)) or bundled single-walled CNTs (FIG. 9($c$)) having a larger particle diameter is/are used (Comparative Examples 1 and 2), CNT 31 cannot pass/receive electrons to/from enzyme 33. On the other hand, with reference to FIG. 9($a$), it is inferred that when debundled single-walled CNTs 31 are used (Example 1), CNT 31 can enter the active center of enzyme 33, and CNT 31 can pass/receive electrons to/from enzyme 33.

Example 2

For Example 2, glucose sensors (of seven types) were fabricated through the same process as in Example 1 except that seven types of FAD-GDHs (enzyme Nos. 1 to 7) shown in Table 1 were used. Note that a case with enzyme No. 1 used overlaps with Example 1. For preparation of the FAD-GDHs, reference can be made for example to Japanese Patent Laying-Open Nos. 2015-167506, 2016-007191, 2016-007192, and 2016-007193.

Example 3

Figure 11:
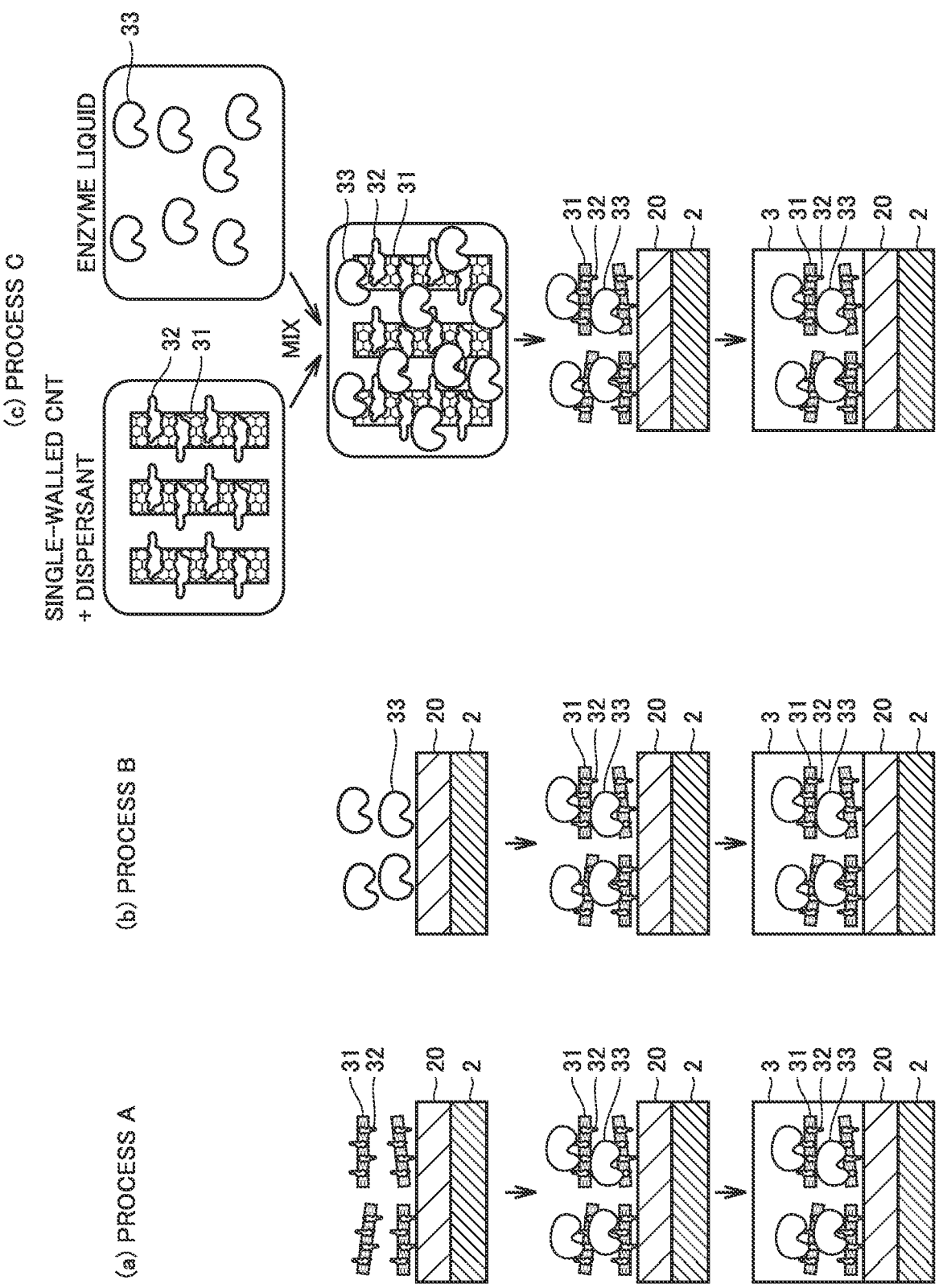
FIG. 11 is a schematic diagram showing a reagent layer formation process (processes A to C).

For Example 3, glucose sensors (of seven types) were fabricated in the same manner as in Example 2 except that instead of the reagent layer formation process (process A) in Example 1, a reagent layer was formed through process B (i.e., applying the enzyme liquid before the CNT liquid (see FIG. 11($b$)).

Example 4

For Example 4, glucose sensors (of seven types) were fabricated in the same manner as in Example 2 except that instead of the reagent layer formation process (process A) in Example 1, a reagent layer was formed through process C (i.e., initially, mixing the CNT liquid and the enzyme liquid together to prepare a liquid mixture and applying it on electrode 2 (hydrophilic polymer membrane 20) (see FIG. 11($c$)).

TABLE 1

| enzyme no. | FAD-GDH gene (derived from) | host | bulk activity (Unit/mg) | Michaelis constant (mM) | molecular weight (kDa) | sensing operation (sensing of current) | | |
|---|---|---|---|---|---|---|---|---|
| | | | | | | Ex. 2 | Ex. 3 | Ex. 4 |
| 1 | Aspergillus terreus var. aureus | Pichia pastoris | 649 | 82 | 110 | + | + | + |
| 2 | Thermoascus crustaceus | Escherichia coli | 181 | 4.6 | 60 | + | − | − |
| 3 | | Pichia pastoris | 88 | 2.8 | 90 | + | + | − |
| 4 | | Saccharomyces cerevisiae | 127 | 3.2 | 90 | + | + | + |
| 5 | Talaromyces emersonii | Escherichia coli | 83 | 406 | 60 | + | − | − |
| 6 | | Pichia pastoris | 28 | 337 | 85 | + | − | − |
| 7 | | Saccharomyces cerevisiae | 32 | 347 | 100 | + | + | − |

Test Example 2

A liquid in which glucose was dissolved in a 20 mM phosphate buffer liquid (pH: 7.4) was prepared as a sample liquid (a glucose liquid) to be measured. The glucose's concentration was 0, 14 or 48 mM.

This sample liquid was supplied into the cavity of each of the glucose sensors (of 21 types in total) fabricated in Examples 2 to 4, and cyclic voltammetry was employed to measure a value of a current, similarly as done for Test Example 1. A result of the measurement is shown in FIGS. 12 and 13.

Figure 12:
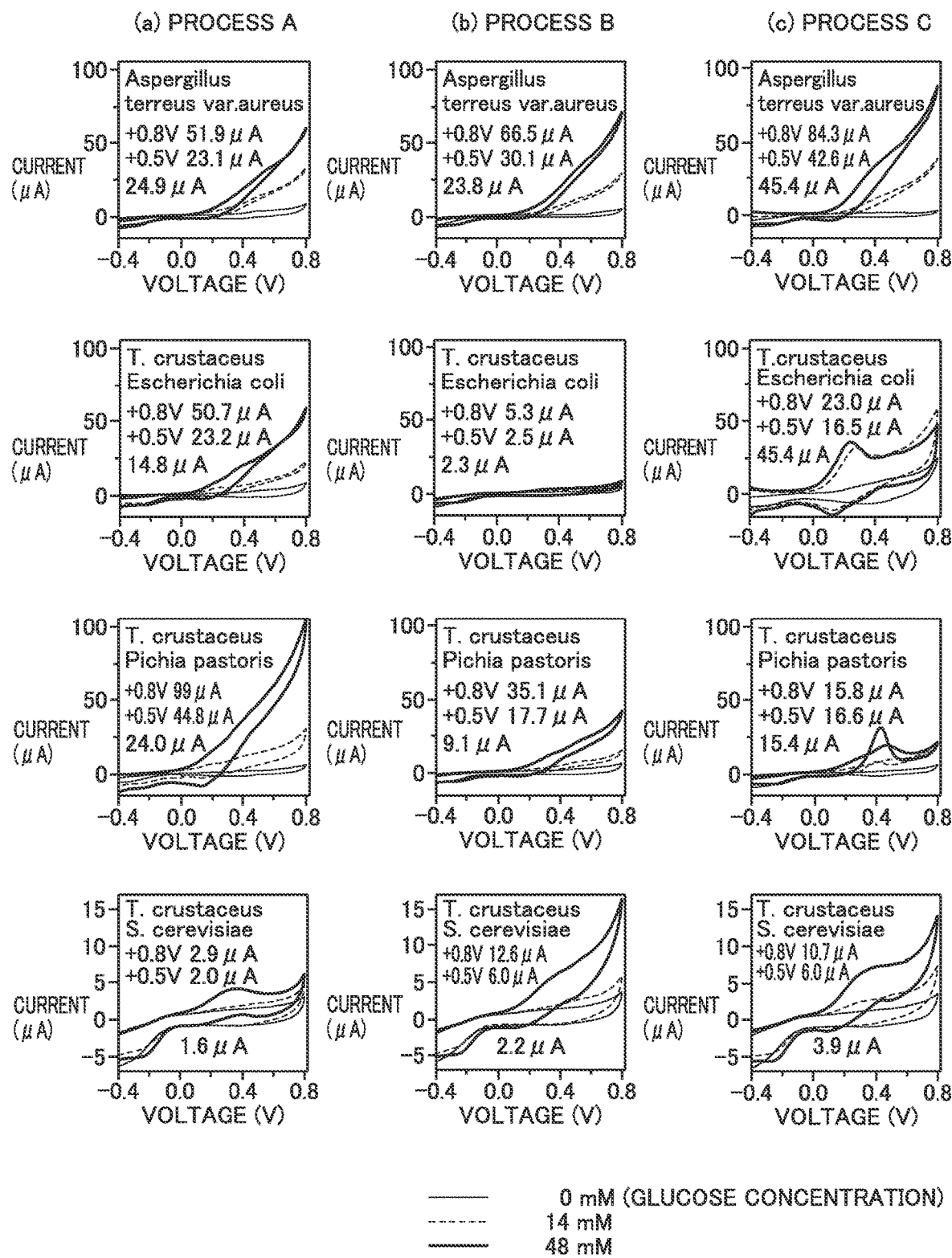
FIG. 12 is a graph showing a result of measuring a value of a current in Test Example 2.

For the measurement results in FIGS. 12 and 13, a result of evaluation of a sensing operation (i.e., whether a current is sensed or not) is shown in Table 1. In Table 1 at the "sensing operation (sensing of current)" column, "+" means that a current is sensed and "−" means that no current is sensed.

From the results shown in Table 1 and FIGS. 12 and 13, it can be seen that a glucose sensor of Example 3 in which the single-walled CNT dispersion liquid was dropped after the enzyme liquid was dropped (Process B) and a glucose sensor of Example 4 in which the enzyme liquid and the single-walled CNT dispersion liquid were mixed together and then dropped (Process C) can steadily sense a current for FAD-GDHs having generally larger apparent molecular weights (that is, having larger amounts of glycosylation).

In particular, it is believed that a FAD-GDH having a molecular weight of 90 kDa or more tends to ensure direct electron transfer between the enzyme and the electrode via the CNT for any of Processes A and B (Examples 2 and 3).

Furthermore, it is believed that a FAD-GDH having a molecular weight of 110 kDa or more tends to ensure direct electron transfer between the enzyme and the electrode via the CNT for any of Processes A, B and C (Examples 2, 3 and 4).

It is believed that Example 2 manufactured through Process A tends to be most reliably sense a current, followed by Example 3 manufactured through Process B followed by Example 4 manufactured through Process C. By thus reliably sensing a current, a highly sensitive and accurate glucose sensor can be provided.

REFERENCE SIGNS LIST

1: insulating substrate; 2: electrode; 20: hydrophilic polymer membrane; 21: working electrode; 22: counter electrode; 3: reagent layer; 31: CNT; 32: dispersant; 33: enzyme; 4: spacer; 41: cavity; 41c: inlet; 42: notch; 5: cover; 5a: air hole; 6: sample liquid.

The invention claimed is:

1. A reagent used for a glucose sensor for electrochemical, quantitative determination of glucose, the reagent consisting of:
   a flavin adenine dinucleotide glucose dehydrogenase;
   single-walled carbon nanotubes configured to allow direct electron transfer between the flavin adenine dinucleotide glucose dehydrogenase and an electrode of the sensor; and
   a dispersant configured to prevent bundling of the single-walled carbon nanotubes.

2. The reagent for a glucose sensor according to claim 1, wherein the flavin adenine dinucleotide glucose dehydrogenase is glycosylated.

3. The reagent for a glucose sensor according to claim 2, wherein the flavin adenine dinucleotide glucose dehydrogenase has a molecular weight of 90 KDa or more.

4. The reagent for a glucose sensor according to claim 3, wherein the flavin adenine dinucleotide glucose dehydrogenase has a molecular weight of 110 KDa or more.

5. The reagent for a glucose sensor according to claim 1, wherein the dispersant includes at least one type of compound selected from an anionic compound, a cationic compound, and a nonionic compound.

6. The reagent for a glucose sensor according to claim 5, wherein the anionic compound is at least any one of sodium dodecyl sulfate, sodium cholate and sodium dodecylbenzene sulfonate.

7. The reagent for a glucose sensor according to claim 5, wherein the cationic compound is cetyltrimethylammonium bromide.

8. The reagent for a glucose sensor according to claim 5, wherein the nonionic compound is at least any one of octylphenol ethoxylate and polysorbates.

9. The reagent for a glucose sensor according to claim 1, wherein the flavin adenine dinucleotide glucose dehydrogenase is derived from *Aspergillus* filamentous fungi, *Thermoascus* filamentous fungi or *Talaromyces* filamentous fungi.

10. A sensor for electrochemical, quantitative determination of glucose, comprising an electrode, the electrode having a surface at least partially covered with a reagent layer comprising a reagent according to claim 1.

11. A method for manufacturing a glucose sensor according to claim 10, the method comprising applying on the electrode a carbon nanotube liquid containing the single-walled carbon nanotubes and the dispersant, followed by an enzyme liquid containing the flavin adenine dinucleotide glucose dehydrogenase, and drying them to form the reagent layer.

12. A method for manufacturing a glucose sensor according to claim 10, the method comprising applying on the electrode an enzyme liquid containing the flavin adenine dinucleotide glucose dehydrogenase, followed by a carbon nanotube liquid containing the single-walled carbon nanotubes and the dispersant, and drying them to form the reagent layer.

13. A method for manufacturing a glucose sensor according to claim 10, the method comprising applying on the electrode a liquid mixture of a carbon nanotube liquid containing the single-walled carbon nanotubes and the dispersant and an enzyme liquid containing the flavin adenine dinucleotide glucose dehydrogenase, and drying it to form the reagent layer.

14. A glucose measuring device comprising the glucose sensor according to claim 10.

* * * * *